(12) United States Patent
Kinoshita et al.

(10) Patent No.: US 8,834,438 B2
(45) Date of Patent: Sep. 16, 2014

(54) SANITARY TAMPON

(75) Inventors: Akie Kinoshita, Kagawa (JP); Masato Isono, Kagawa (JP); Koichi Yamaki, Kagawa (JP); Hitoshi Watanabe, Kagawa (JP)

(73) Assignee: Uni-Charm Corporation, Ehime-ken (JP)

( * ) Notice: Subject to any disclaimer, the term of this patent is extended or adjusted under 35 U.S.C. 154(b) by 456 days.

(21) Appl. No.: 13/203,607

(22) PCT Filed: Feb. 22, 2010

(86) PCT No.: PCT/JP2010/052627
§ 371 (c)(1),
(2), (4) Date: Oct. 31, 2011

(87) PCT Pub. No.: WO2010/098280
PCT Pub. Date: Sep. 2, 2010

(65) Prior Publication Data
US 2012/0053550 A1    Mar. 1, 2012

(30) Foreign Application Priority Data
Feb. 27, 2009   (JP) ................. 2009-047328

(51) Int. Cl.
| | |
|---|---|
| *A61F 13/20* | (2006.01) |
| *A61F 13/34* | (2006.01) |
| *A61F 13/537* | (2006.01) |
| *A61F 13/513* | (2006.01) |
| *A61F 13/15* | (2006.01) |

(52) U.S. Cl.
CPC ....... *A61F 13/2031* (2013.01); *A61F 13/53708* (2013.01); *A61F 2013/15422* (2013.01); *A61F 13/2071* (2013.01); *A61F 13/51305* (2013.01)
USPC ................. 604/385.17; 604/385.18

(58) Field of Classification Search
CPC   A61F 13/2071; A61F 13/53708; A61F 13/51
USPC ....................... 604/385.17–385.18
See application file for complete search history.

(56) References Cited

U.S. PATENT DOCUMENTS 3,055,369 A * 9/1962 Graham, Jr. .................. 604/15
6,118,042 A * 9/2000 Palumbo ...................... 604/368

(Continued)

FOREIGN PATENT DOCUMENTS

| CN | 1229350 A | 9/1999 |
| EP | 531096 A2 * | 3/1993 |

(Continued)

OTHER PUBLICATIONS

International Search Report for PCT/JP2010/052627 dated May 25, 2010.

(Continued)

*Primary Examiner* — Susan Su
(74) *Attorney, Agent, or Firm* — Lowe Hauptman & Ham

(57) ABSTRACT

The covering member includes an inner side surface being in contact with the absorber and an outer side surface to come into contact with a vaginal wall when in use. The covering member contains a hydrophobic fiber with a low affinity to water and a hydrophilic fiber with a high affinity to water. In the outer side surface, an abundance ratio of the hydrophobic fiber is higher than an abundance ratio of the hydrophilic fiber.

6 Claims, 7 Drawing Sheets

(56) References Cited

U.S. PATENT DOCUMENTS

| | | | |
|---|---|---|---|
| 6,465,713 B1 | 10/2002 | Gell et al. | |
| 6,719,743 B1 | 4/2004 | Wada | |
| 7,977,532 B2* | 7/2011 | Hasse et al. | 604/381 |
| 2002/0016122 A1* | 2/2002 | Curro et al. | 442/381 |
| 2002/0142693 A1* | 10/2002 | Buzot | 442/414 |
| 2005/0148969 A1 | 7/2005 | Damay et al. | |
| 2008/0177241 A1* | 7/2008 | Hasse et al. | 604/379 |
| 2011/0217894 A1* | 9/2011 | Coslett et al. | 442/382 |
| 2012/0101462 A1* | 4/2012 | Lee | 604/379 |

FOREIGN PATENT DOCUMENTS

| | | | | |
|---|---|---|---|---|
| JP | 6227952 A | | 2/1987 | |
| JP | 62-144658 A | | 6/1987 | |
| JP | 62-108920 U | | 7/1987 | |
| JP | 1146548 | * | 6/1989 | A61F 13/20 |
| JP | 1146548 A | | 6/1989 | |
| JP | 5-068695 A | | 3/1993 | |
| JP | 7328064 A | | 12/1995 | |
| JP | 2001008964 A | | 1/2001 | |
| JP | 2002514961 A | | 5/2002 | |
| JP | 2005537860 A | | 12/2005 | |

OTHER PUBLICATIONS

Office Action issued Jul. 12, 2013 corresponds to Eurasian patent application No. 201101216.
Extended European Search Report corresponding to EP10746161.8, dated Mar. 13, 2013.
Office Action corresponding to JP2009-047328, dated Jan. 29, 2013.
Chinese Office Action issued on Apr. 24, 2013 in counterpart Chinese Patent Application No. 201080009785.9.
Office Action mailed Oct. 8, 2013, corresponds to Japanese patent application No. 2009-047328.
US 6,353,147, 03/2002, Foley et al. (withdrawn)

* cited by examiner

SANITARY TAMPON

RELATED APPLICATIONS

The present application is a national phase application based on PCT/JP10/052,627, filed Feb. 22, 2010 and is based on, and claims priority from, Japanese Application Number 2009-047328, filed Feb. 27, 2009.

TECHNICAL FIELD

The present invention relates to a sanitary tampon including an absorber having an absorbent fiber and a covering member covering the absorber.

BACKGROUND ART

A sanitary tampon includes an absorber capable of absorbing body fluids and a covering member covering the absorber, and is inserted into the vagina of a user to absorb body fluids such as menstrual blood.

As such a sanitary tampon, a sanitary tampon including an absorber layer having an absorbent fiber covered with a hydrophobic liquid-permeable layer to form an absorber is known (see, for example, Patent Literature 1).

PRIOR ART DOCUMENT

Patent Literature

[Patent Literature 1]
Japanese Patent Application Publication No. 2001-8964

SUMMARY OF INVENTION

However, the above-described conventional sanitary tampon has the following problem. Specifically, having hydrophobic properties, the surface of the absorber (the liquid-permeable layer) to come into contact with a vaginal wall worsens the ability of the absorber to absorb body fluids such as menstrual blood. For this reason, the body fluids tend to easily flow on the surface of the absorber, thus sometimes causing leakage of the menstrual blood and wearing discomfort.

A way to improve the ability of the absorber to absorb body fluids is to make the surface of the absorber hydrophilic. However, if the surface of the absorber is made hydrophilic, the absorber excessively absorbs body fluids existing on the vaginal wall surface. This causes a phenomenon that the surface of the absorber sticks to the vaginal wall. Such phenomenon increases the frictional resistance generated when the sanitary tampon is inserted or taken out after use, which causes a user to feel uncomfortable.

Accordingly, an object of the present invention is to provide a sanitary tampon having an improved ability to absorb body fluids such as menstrual blood and being prevented from sticking to a vaginal wall.

To solve the aforementioned problems, an aspect of the present invention is a sanitary tampon including: an absorber having an absorbent fiber; and a covering member covering the absorber. In the sanitary tampon, the covering member includes: an inner side surface being in contact with the absorber; and an outer side surface to come into contact with a vaginal wall when in use, the covering member contains a hydrophilic fiber with a high affinity to water and a hydrophobic fiber with a low affinity to water, an abundance ratio of the hydrophobic fiber in the outer side surface is higher than an abundance ratio of the hydrophilic fiber in the outer side surface, and the inner side surface is made of the hydrophilic fiber.

According to the present invention, it is possible to provide a sanitary tampon having an improved ability to absorb body fluids such as menstrual blood and being prevented from sticking to a vaginal wall.

DESCRIPTION OF EMBODIMENTS

Figure 1:
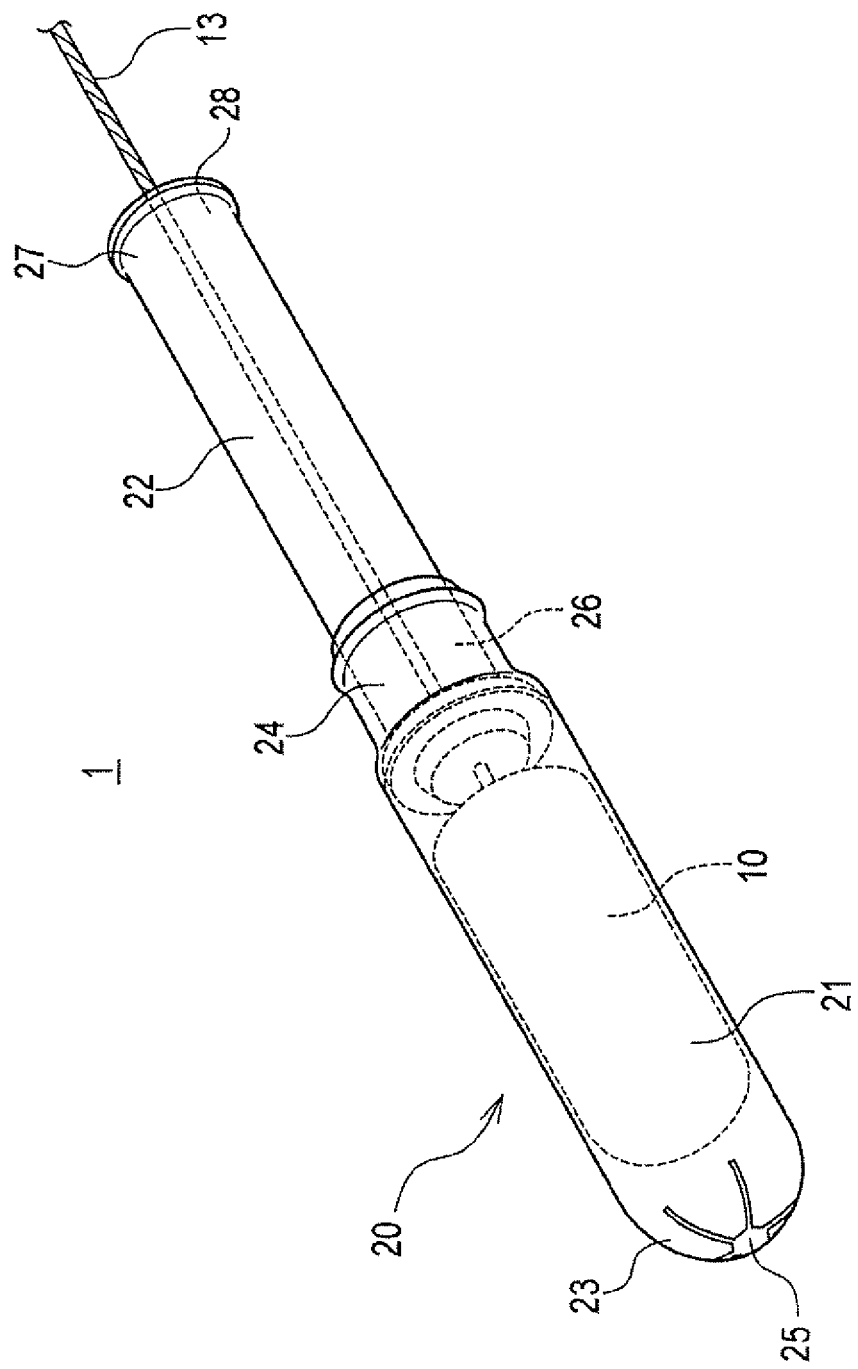
FIG. 1 is a perspective view of a sanitary tampon according to a first embodiment of the present invention.

Embodiments of a sanitary tampon according to the present invention will be described by referring to the drawings. In the following description of the drawings, same or similar reference numerals denote same or similar elements and portions. In addition, it should be noted that the drawings are schematic and ratios of dimensions and the like are different from actual ones.

Therefore, specific dimensions and the like should be determined in consideration of the following description. Moreover, the drawings also include portions having different dimensional relationships and ratios from each other.

First Embodiment

FIG. 1 is a perspective view of a sanitary tampon 1. The sanitary tampon 1 includes an absorber body 10 and an applicator 20 housing the absorber body 10.

The applicator 20 includes an outer tube 21 housing the absorber body 10 to be electable therefrom and a pushing body 22 pushing the absorber body 10.

The outer tube 21 includes an outer tube front end 23 which is inserted into the vagina of a user and an outer tube rear end 24 which is located opposite to the outer tube front end 23. The outer tube front end 23 has an opening portion 25 through which the absorber body 10 is ejected.

The pushing body 22 includes a pushing front end 26 which pushes the absorber body 10 toward the outside of the outer tube 21 and a pushing rear end 27 which is located opposite to the pushing front end 26.

The pushing body 22 has a continuous hole 28 communicating with the pushing front end 26 and the pushing rear end 27. A cord 13 (to be described later) connected with the absorber body 10 passes through the continuous hole 28.

When the pushing rear end 27 is pushed toward the outer tube front end 23, the pushing front end 26 slides inside the outer tube 21 and thereby pushes the absorber body 10 toward the outside of the outer tube 21. The opening portion 25 is pushed and stretched by the absorber body 10, so that the absorber body 10 is ejected through the opening portion 25 to the outside of the outer tube 21.

Figure 2:
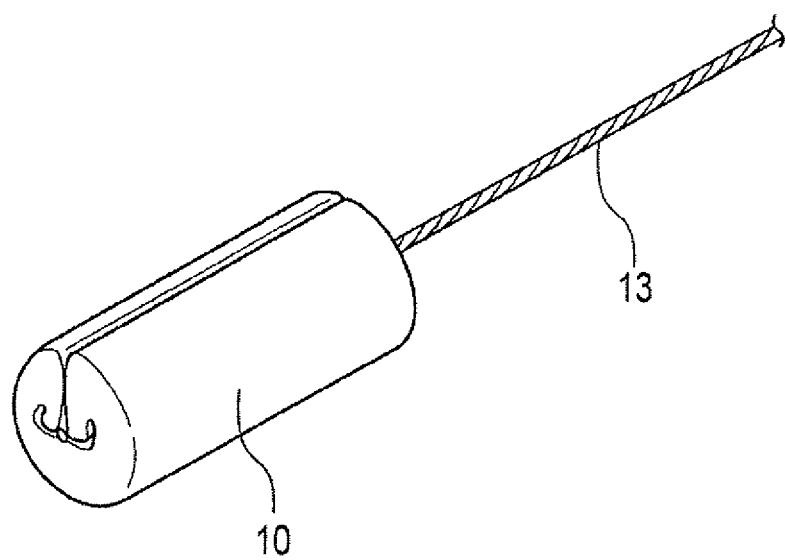
FIG. 2 is a perspective view of an absorber body according to the first embodiment of the present invention.
Figure 3:
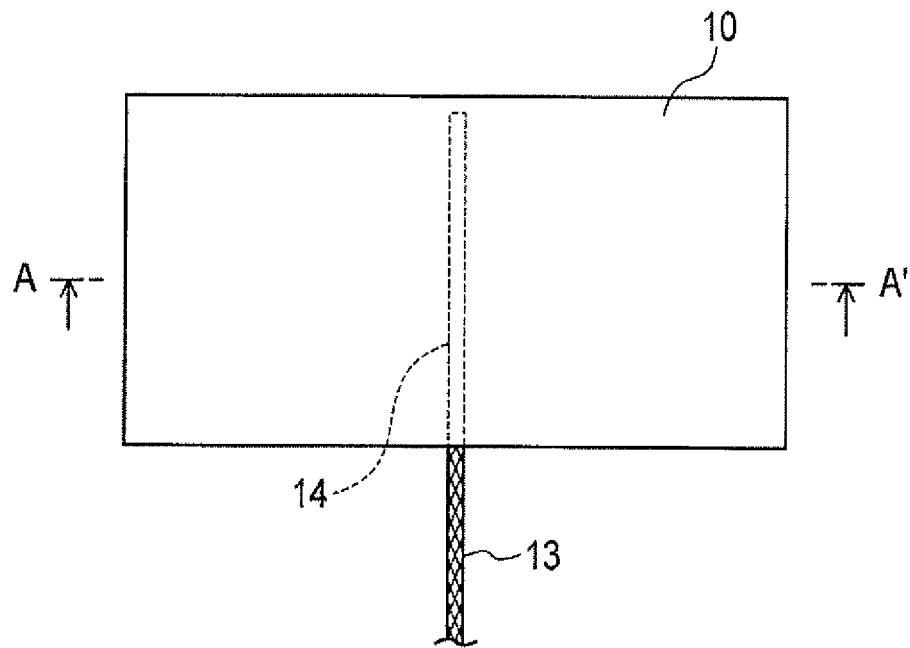
FIG. 3 is an exploded plan view of the absorber body according to the first embodiment.

FIG. 2 is a perspective view of the absorber body 10. FIG. 3 is an exploded plan view of the absorber body 10. The absorber body 10 has a sheet shape and is housed inside the outer tube 21 in a compressed state.

The absorber body 10 has a connection portion 14 in a predetermined position. In the first embodiment, the predetermined position is the center portion of the absorber body 10. The cord 13 is sewed with a thread 15 into the absorber body 10 in the connection portion 14.

Figure 4:
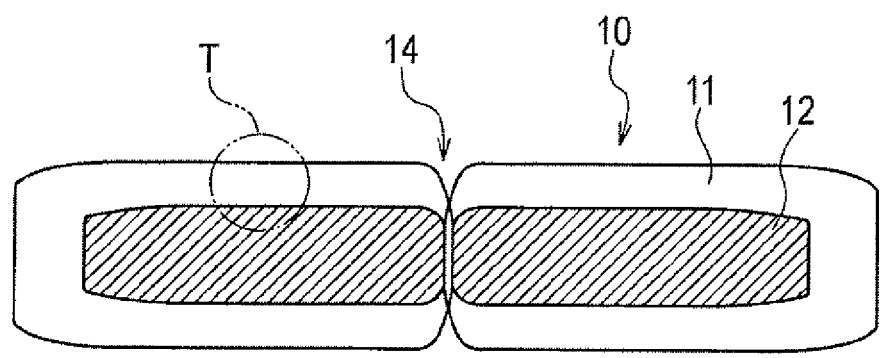
FIG. 4 is a cross-sectional view taken along the A-A' line in FIG. 3.

FIG. 4 is a cross-sectional view showing a cross-section taken along the A-A' line in FIG. 3. The absorber body 10 includes an absorber 12 having an absorbent fiber and a covering member 11 covering the absorber 12. End portions of the covering member 11 overlap with each other in the connection portion 14. The covering member 11, the absorber 12, and the cord 13 are sewed together with a thread 15 in the connection portion 14.

Figure 5:
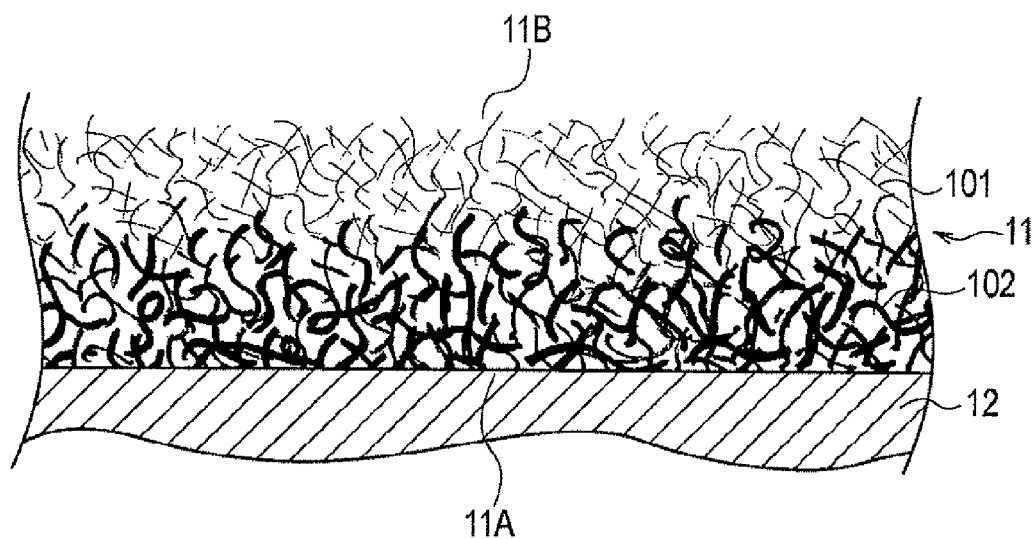
FIG. 5 is an enlarged view of a covering member and an absorber of the sanitary tampon according to the first embodiment of the present invention.

FIG. 5 is an enlarged view of a region T in the cross-section of FIG. 4. As shown in FIG. 5, the covering member 11 includes an inner side surface 11A being in contact with the absorber 12 and an outer side surface 11B to come into contact with a vaginal wall when in use. The covering member 11 contains a hydrophobic fiber 101 with a low affinity to water and a hydrophilic fiber 102 with a high affinity to water.

The abundance ratio of the hydrophobic fiber 101 in the outer side surface 11B is higher than that of the hydrophilic fiber 102 in the outer side surface 11B. It is preferable that the compounding ratio of the hydrophilic fiber 102 in the outer side surface 11B be 10 to 50% of the total volume of the covering member 11.

If the compounding ratio of the hydrophilic fiber 102 in the outer side surface 11B is equal to or less than 10%, the affinity of the covering member 11 in the outer side surface 11B to water is reduced. For this reason, menstrual blood having adhered to the absorber body 10 is more likely to flow down on the outer side surface 11B of the absorber body 10 than to move from the outer side surface 11B to the inner side surface 11A. As a result, the menstrual blood tends to easily leak through a vaginal opening.

On the other hand, if the compounding ratio of the hydrophilic fiber 102 in the outer side surface 11B is equal to or higher than 50%, the affinity of the covering member 11 in the outer side surface 11B to water is increased. In this case, the outer side surface 11B absorbs a small amount of menstrual blood located on the vaginal wall, and thus the outer side surface 11B sticks to the vaginal wall. This causes a user to feel pain or a sense of discomfort when the absorber body 10 is taken out.

The covering member 11 may be a nonwoven fabric such as a spunbonded nonwoven fabric, a point-bonded nonwoven fabric, or an air permeable nonwoven fabric, which is manufactured by a general method of manufacturing a nonwoven fabric. More preferably, in the first embodiment, the covering member 11 is a spunlace nonwoven fabric in which the hydrophobic fiber 101 and the hydrophilic fiber 102 are entangled by the hydroentangling method. The spunlace nonwoven fabric is manufactured by entangling fibers with one another by using jets of water. Thus, there is no clear boundary between a fiber layer made of the hydrophobic fiber 101 and a fiber layer made of the hydrophilic fiber 102. This helps body fluids quickly move from the outer side surface 11B to the inner side surface 11A. Also, the spunlace nonwoven fabric is advantageous in that there is no residue of an oil solution from raw cotton.

It is preferable that the hydrophobic fiber 101 be a synthetic fiber such as polyester, polyolefin, polyamide or polyacryl, or a mixture of these fibers. In addition, the absorber body 10 becomes one of high temperature and high pressure when housed in the outer tube 21 in a compressed state. Therefore, it is preferable that a melting point be equal to or higher than 130° C. and a breaking strength (JISL1096) of the nonwoven fabric be 12 mN/25 mm.

The hydrophilic fiber 102 may be a fiber which is generally used as an absorbent material, such as rayon (including conventional normal rayon and atypical rayon), cotton, grind wood pulp, wool, silk, a cellulose fiber which is chemically denatured, modified, or cross-linked, a synthetic fiber, tissue, or peat moss. Also, a mixture of these fibers may be used. It is preferable that the hydrophilic fiber 102 be made of a material same as that of the absorber 12 as described later. The use of the same material for the hydrophilic fiber 102 and the absorber 12 allows the hydrophilic fiber 102 and the fiber of the absorber 12 to be fitted well together, so that body fluids such as menstrual blood can be easily guided to the absorber 12.

It is preferable that the diameter of each of the hydrophobic fiber 101 and the hydrophilic fiber 102 be 1.7 to 3.3 deniers. If the fiber diameter is equal to or larger than 3.3 deniers, a stiffness of one fiber becomes high, which results in an unpleasant sense of touch for a user. In contrast, if the fiber diameter is equal to or smaller than 1.7 deniers, it becomes difficult to manufacture the fiber with a stable thickness.

The inner side surface 11A is made of the hydrophilic fiber 102. A weight per unit area (also referred to as a basic weight) of the hydrophilic fiber 102 is equal to or larger than a weight per unit area of the hydrophobic fiber 101.

A basic weight of the hydrophobic fiber 101 forming the outer side surface 11B of the covering member 11 is 8 to 20 g/m$^2$. It is also preferable that a basic weight of the hydrophilic fiber 102 forming the inner side surface 11A be 8 to 40 g/m$^2$. If the basic weight is equal to or smaller than 8 g/m$^2$, the amount of fibers in spread raw cotton is too small to manufacture a web with a stable amount of fibers.

If the basic weight of the hydrophobic fiber 101 exceeds 20 g/m$^2$, menstrual blood having adhered to the absorber body 10 is more likely to flow down on the outer side surface 11B of the absorber body 10 than to move from the outer side surface 11B to the inner side surface 11A. As a result, the menstrual blood tends to easily leak through a vaginal opening.

If the basic weight of the hydrophilic fiber 102 exceeds 40 g/m$^2$, the stiffness of the covering member 11 is so high that the absorber body 10 inserted into the vagina is prevented from being restored from a compressed state to a ready-to-use state.

The absorber 12 may be a fiber which is generally used as an absorbent material, such as rayon (including conventional normal rayon and atypical rayon), cotton, grind wood pulp, wool, silk, a cellulose fiber which is chemically denatured, modified, or cross-linked, a synthetic fiber, tissue, or peat moss. Also, a mixture of these fibers may be used. The absorber 12 may include an absorbent polymer and an absorbent gel as a mixture. It is preferable that the basic weight of the absorber 12 be 100 to 1200 g/m$^2$.

The cord 13 is formed of a single yarn including, for example, rayon, cotton, polyethylene or polypropylene, or a conjugated yarn which is a strand of these yarns. It is preferable that the cord 13 be finished with paraffin, for example, to provide a water repellent property thereto so as to prevent the cord 13 from getting dirty by menstrual blood or body fluids.

The absorber body 10 is housed in the outer tube 21 in a compressed state. In a process of forming the absorber body 10 in such a size that the absorber body 10 can be housed in the outer tube 21, the absorber body 10 is subjected to compression molding using a substantially cylindrical mold having multiple projected portions in the longitudinal direction. Alternatively, the absorber body 10 is subjected to compression molding to have a regulated size by being pressed both from a conveying direction (MD direction) and a cross direction (CD direction).

It is preferable that the size of the absorber body 10 in the length direction after the absorber body 10 is compressed be 30 to 60 mm. If the size of the absorber body 10 in the length direction after the absorber body 10 is compressed is equal to or smaller than 30 mm, an area of the absorber body 10 which comes in contact with the vaginal wall is so small that menstrual blood cannot be sufficiently absorbed. If the size of the absorber body 10 in the length direction after the absorber body 10 is compressed exceeds 60 mm, the absorber body 10 is swollen to reach the vicinity of the vaginal opening once absorbing menstrual blood or the like. As a result, a user feels a sense of discomfort.

If the size of the absorber body 10 in the length direction after the absorber body 10 is formed by compression molding is 30 mm to 60 mm, it is preferable that the length of the cord 13 be in a range from 150 mm to 250 mm. If the length of the cord 13 is equal to or smaller than 150 mm, it is difficult for a user to find the cord 13 when the user tries to take out the absorber body 10. In addition, if the length of the cord 13 exceeds 250 mm, the absorber body 10 having been taken out may come into contact with the wear of the user or a toilet bowl and make it dirty.

As described above, in the sanitary tampon 1 according to the first embodiment of the present invention, the covering member 11 includes the hydrophobic fiber 101 with a low affinity to water and the hydrophilic fiber 102 with a high affinity to water. The abundance ratio of the hydrophobic fiber 101 in the outer side surface 11B is higher than that of the hydrophilic fiber 102 in the outer side surface 11B.

With this structure, body fluids such as menstrual blood moving on the hydrophobic fiber 101 in the outer side surface 11B penetrate through the hydrophilic fiber 102 forming the outer side surface 11B. The body fluids having penetrated through the hydrophilic fiber 102 forming the outer side surface 11B then penetrate through the hydrophilic fiber 102 forming the inner side surface 11A. In other words, the hydrophilic fiber 102 forming the inner side surface 11A also functions as the absorber 12. Accordingly, the absorbency of the sanitary tampon 1 can be improved.

The body fluids having penetrated through the hydrophilic fiber 102 forming the inner side surface 11A hardly return to the surface of the outer side surface 11B (the vaginal wall side) by being inhibited by the hydrophobic fiber 101 forming the outer side surface 11B. The body fluids having penetrated through the hydrophilic fiber 102 forming the inner side surface 11A are absorbed by the absorber 12 being in contact with the inner side surface 11A. Accordingly, the ability to absorb the body fluids can be improved.

In the first embodiment, the abundance ratio of the hydrophobic fiber 101 is higher in the outer side surface 11B. Thus, the surface of the covering member 11 is more likely to take on the property of the hydrophobic fiber 101. This prevents the absorber body 10 from sticking to the vaginal wall.

In the first embodiment, the basic weight of the hydrophilic fiber 102 is larger than that of the hydrophobic fiber 101. In other words, the fiber layer made of the hydrophilic fiber 102 has a thickness larger than that of the fiber layer made of the hydrophobic fiber 101. Since the amount of the hydrophilic fiber 102 is large, the covering member 11 per se can absorb the body fluids and is fitted well with the absorber 12.

In the first embodiment, the covering member 11 is a spunlace nonwoven fabric in which the hydrophobic fiber 101 and the hydrophilic fiber 102 are entangled by the hydroentangling method. In other words, the hydrophobic fiber 101 which mainly forms the outer side surface 11B and the hydrophilic fiber 102 forming the inner side surface 11A are entangled with each other in the thickness direction of the covering member 11. Accordingly, flow paths from the outer side surface 11B to the inner side surface 11A are formed. This helps body fluids easily penetrate through the covering member 11 from the outer side surface 11B to the inner side surface 11A.

Second Embodiment

Figure 6:
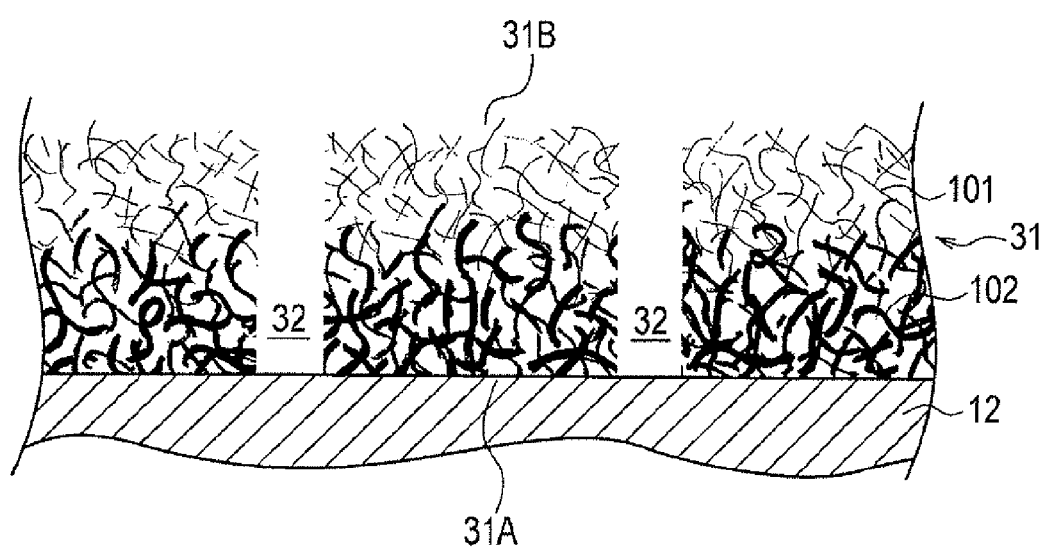
FIG. 6 is an enlarged view of a covering member and an absorber of a sanitary tampon according to a second embodiment of the present invention.

A second embodiment of the present invention is described below. In the second embodiment, the structure of a covering member covering an absorber is different from that of the first embodiment. In the following description, portions different from the first embodiment are described. Similar to FIG. 5, FIG. 6 is a partially enlarged view of an absorber and a covering member covering the absorber. In the second embodiment, a covering member 31 is used in place of the covering member 11.

The covering member 31 includes an inner side surface 31A being in contact with an absorber 12 and an outer side surface 31B to come into contact with a vaginal wall when in use. The covering member 31 includes a hydrophobic fiber 101 with a low affinity to water and a hydrophilic fiber 102 with a high affinity to water. An abundance ratio of the hydrophobic fiber 101 in the outer side surface 31B is higher than that of the hydrophilic fiber 102 in the outer side surface 31B. The inner side surface 31A is made of the hydrophilic fiber 102. As shown in FIG. 6, the covering member 31 has through holes 32 formed therein. The through holes 32 pass through the outer side surface 31B and the inner side surface 31A.

With the covering member 31 shown in the second embodiment, body fluids tend to easily move to the absorber 12 along the through holes 32 formed in the covering member 31. Thus, the absorbency is improved.

Third Embodiment

Figure 7:
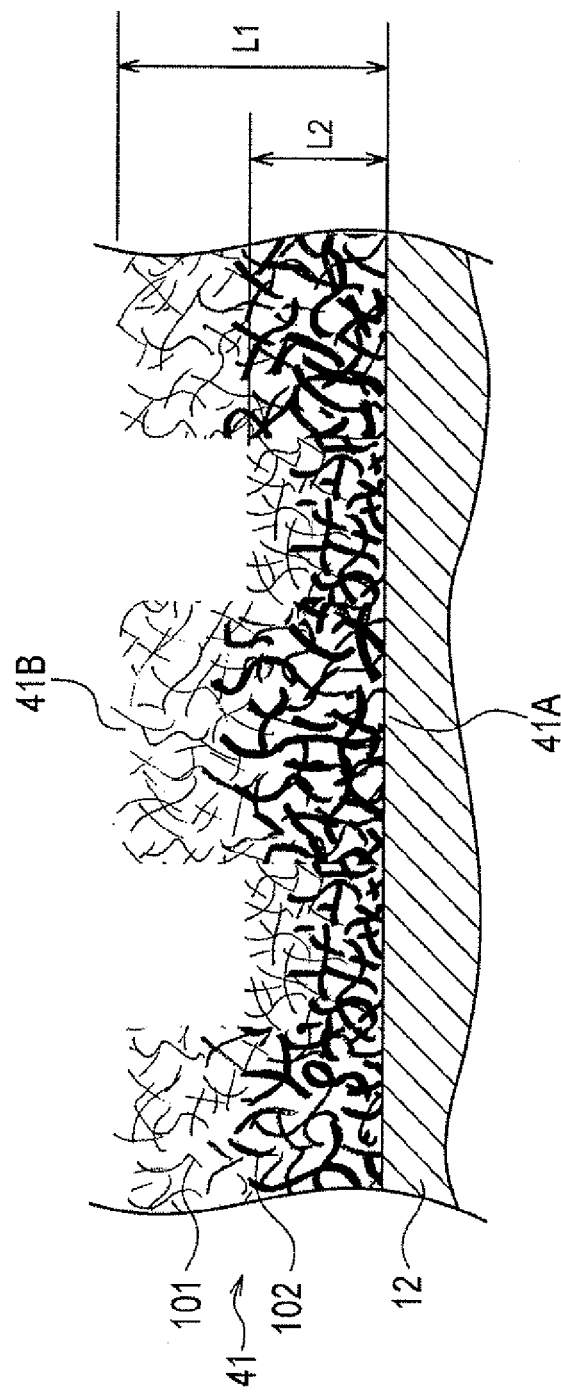
FIG. 7 is an enlarged view of a covering member and an absorber of a sanitary tampon according to a third embodiment of the present invention.

A third embodiment of the present invention is described below. In the third embodiment, the structure of a covering member covering an absorber is different from those of the first and second embodiments. In the following description, portions different from the first and second embodiments are described. Similar to FIG. 5, FIG. 7 is a partially enlarged view of an absorber and a covering member covering the absorber. In the third embodiment, a covering member 41 is used in place of the covering member 11.

The covering member 41 includes an inner side surface 41A being in contact with an absorber 12 and an outer side surface 41B to come into contact with a vaginal wall when in use. The covering member 41 includes a hydrophobic fiber 101 with a low affinity to water and a hydrophilic fiber 102 with a high affinity to water. An abundance ratio of the hydrophobic fiber 101 in the outer side surface 41B is higher than that of the hydrophilic fiber 102 in the outer side surface 41B. The inner side surface 41A is made of the hydrophilic fiber 102.

A part of the covering member 41 is of different thickness. Specifically, as shown in FIG. 7, the covering member 41 has a thickness L1 in some portions and a thickness L2 in other portions, where L1>L2. Here, a method of forming portions having different layer thicknesses includes a method of forming portions having different thicknesses in the step of manufacturing the covering member 41. In the manufacturing step, a pattern plate in which a projected portion corresponding to a portion of thin layer thickness is provided is used and raw materials are stacked in the pattern plate.

With the covering member 41 shown in the third embodiment, body fluids easily penetrate through the covering member 41 from the portions of thickness L1 to the portions of thickness L2. Accordingly, the absorbency is improved.

Fourth Embodiment

Figure 8:
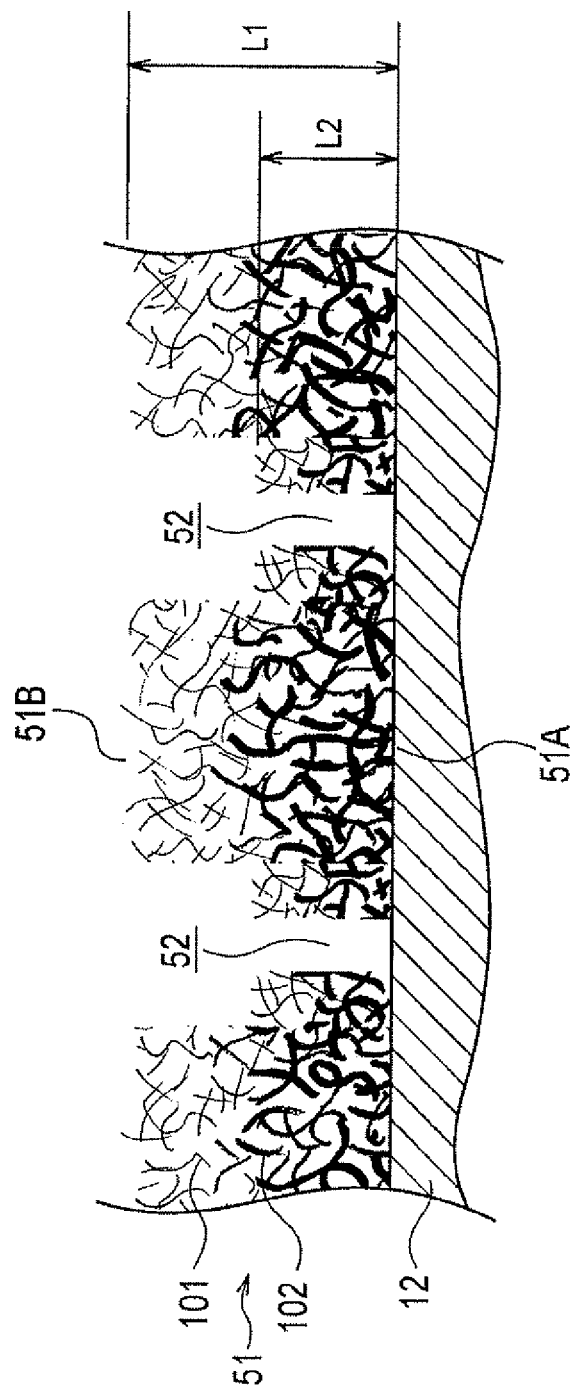
FIG. 8 is an enlarged view of a covering member and an absorber of a sanitary tampon according to a fourth embodiment of the present invention.

A fourth embodiment of the present invention is described below. In the fourth embodiment, the structure of a covering member covering an absorber is different from those of the first to third embodiments. In the following description, portions different from the first to third embodiments are described. Similar to FIG. 5, FIG. 8 is a partially enlarged view of an absorber and a covering member covering the absorber. In the fourth embodiment, a covering member 51 is used in place of the covering member 11.

The covering member 51 has through holes 52 formed in portions of thickness L2 (thinner than other portions) in the covering member 41 a part of which is of different thickness as described in the third embodiment.

Specifically, the covering member 51 includes an inner side surface 51A being in contact with an absorber 12 and an outer side surface 51B to come into contact with a vaginal wall when in use. The covering member 51 includes a hydrophobic fiber 101 with a low affinity to water and a hydrophilic fiber 102 with a high affinity to water. An abundance ratio of the hydrophobic fiber 101 in the outer side surface 51B is higher than that of the hydrophilic fiber 102 in the outer side surface 51B. The inner side surface 51A is made of the hydrophilic fiber 102.

A part of the covering member 51 is of different thickness. Specifically, as shown in FIG. 8, the covering member 51 has a thickness L1 in some portions and a thickness L2 in other portions, where L1>L2. The covering member 51 also has through holes 52 formed in the portions of thickness L2.

With the covering member 51 shown in the fourth embodiment, body fluids tend to easily penetrate through the covering member 51 from the portions of thickness L1 to the portions of thickness L2. Also, the body fluids tend to easily move to the absorber 12 along the through holes 52 formed in the covering member 51. Thus, the absorbency is improved.

Fifth Embodiment

Figure 9:
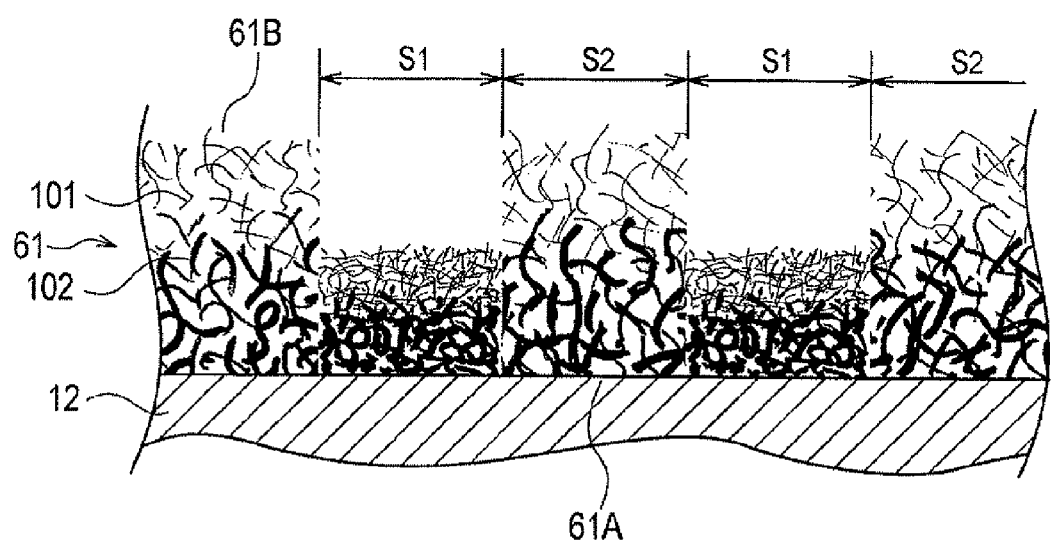
FIG. 9 is an enlarged view of a covering member and an absorber of a sanitary tampon according to a fifth embodiment of the present invention.

A fifth embodiment of the present invention is described below. In the fifth embodiment, the structure of a covering member covering an absorber is different from those of the first to fourth embodiments. In the following description, portions different from the first to fourth embodiments are described. Similar to FIG. 5, FIG. 9 is a partially enlarged view of an absorber and a covering member covering the absorber. In the fifth embodiment, a covering member 61 is used in place of the covering member 11. The covering member 61 has portions whose fiber density is relatively high and portions whose fiber density is relatively low.

Specifically, the covering member 61 includes an inner side surface 61A being in contact with an absorber 12 and an outer side surface 61B to come into contact with a vaginal wall when in use. The covering member 61 includes a hydrophobic fiber 101 with a low affinity to water and a hydrophilic fiber 102 with a high affinity to water. An abundance ratio of the hydrophobic fiber 101 in the outer side surface 61B is higher than that of the hydrophilic fiber 102 in the outer side surface 61B. The inner side surface 61A is made of the hydrophilic fiber 102.

As shown in FIG. 9, regions S1 in the covering member 61 are portions whose fiber density is relatively high. On the other hand, regions S2 are portions whose fiber density is relatively low.

With the covering member 61 shown in the fifth embodiment, body fluids tend to easily penetrate through the covering member 61 from the portions whose fiber density is low to the portions whose fiber density is high. Thus, the absorbency is improved. In the fifth embodiment, the covering member 61 may have through holes in the portions whose fiber density is high. Here, a method of forming portions having different layer thicknesses includes a method of partially changing a water pressure during embossing or spunlacing.

Other Embodiments

The present invention has been described in detail by using the above-described embodiments. However, it is obvious for a person skilled in the art that the present invention is not limited to the embodiments described herein. The present invention can be modified and embodied as alternative embodiments without departing from the gist and scope of the present invention which is defined by the appended claims. Accordingly, the description herein is for illustrative purpose only and not intended to limit the present invention.

In the above-described embodiments, the description is given of the case where the cord 13 is sewed into the absorber body 10 in the connection portion 14. However, the cord 13 may be formed in such a manner that end portions of threads used for sewing together the covering member 11 and the absorber 12 are extended toward the outside of the absorber body 10 and entangled. In this case, the cord 13 can be used not only for integrating together the covering member 11 and the absorber 12 but also for pulling out the absorber body 10 after use from the vaginal opening. Thus, it is advantageous that problems such as breaking of a sewing thread and a stitch defect are prevented from occulting, so that the cord is prevented from coming off from the absorber body 10.

In the embodiments, the description is given of the case where the cord 13 is connected in the center portion. However, the cord 13 may be connected in an end portion of the absorber body 10.

The hydrophilic fiber 102 may be a fiber to which the affinity to water is provided by performing a proper process on a fiber with a low affinity to water.

A spunlace nonwoven fabric is described as a preferable example of the covering member in the embodiments. However, the covering member is not limited to the spunlace nonwoven fabric. For example, the covering member may be a fabric formed by laminating and integrating two sheets of nonwoven fabrics. Specifically, a spunbonded nonwoven fabric in which a hydrophobic fiber and a hydrophilic fiber are mixed is placed as an outer side surface and a nonwoven fabric in which rayon is mixed with a heat seal fiber is placed as an inner side surface, which are subjected to the hot embossing to obtain an integrated nonwoven fabric. With such a nonwoven fabric, the spunbonded nonwoven fabric on the outer side surface prevents the outer side surface from sticking to the vaginal wall and the nonwoven fabric in which rayon is mixed with the heat seal fiber facilitates the movement of liquid to the absorber.

Note that the entire content of Japanese Patent Application No. 2009-047328 (filed on Feb. 27, 2009) is incorporated by reference into this application.

INDUSTRIAL APPLICABILITY

Since the present invention is capable of providing a sanitary tampon having an improved ability to absorb body fluids such as menstrual blood and being prevented from sticking to a vaginal wall, it is useful in manufacturing of the sanitary tampons.

REFERENCE SIGNS LIST

1: sanitary tampon, 10: absorber body, 11: covering member, 11A: inner side surface, 11B: outer side surface, 12: absorber, 13: cord, 14: connection portion, 20: applicator, 21: outer tube, 22: pushing body, 23: outer tube front end, 24: outer tube rear end, 25: opening portion, 26: pushing front end, 27: pushing rear end, 28: continuous hole, 31: covering member, 31A: inner side surface, 31B: outer side surface, 32: through hole, 41: covering member, 41A: inner side surface, 41B: outer side surface, 51: covering member, 51A: inner side surface, 51B: outer side surface, 52: through hole, 61: covering member, 61A: inner side surface, 61B: outer side surface, 101: hydrophobic fiber, 102: hydrophilic fiber

The invention claimed is:

1. A sanitary tampon, comprising:
an absorber having an absorbent fiber; and
a covering member covering the absorber,
wherein
the covering member includes:
an inner side surface being in contact with the absorber; and
an outer side surface configured to come into contact with a vaginal wall when in use,
the covering member includes hydrophilic fibers and hydrophobic fibers,
on the outer side surface, an abundance ratio of the hydrophobic fibers is higher than an abundance ratio of the hydrophilic fibers,
the inner side surface is made of the hydrophilic fibers,
a thickness of first portions of the covering member is non-zero and is less than a thickness of second portions of the covering member, and
the first portions of the covering member include through holes passing through the covering member from the outer side surface to the inner side surface.

2. The sanitary tampon according to claim 1, wherein a weight per unit area of the hydrophilic fibers is not less than a weight per unit area of the hydrophobic fibers.

3. The sanitary tampon according to claim 1, wherein the covering member is a spunlace nonwoven fabric in which the hydrophilic fibers and the hydrophobic fibers are entangled by a hydroentangling method.

4. The sanitary tampon according to claim 1, wherein the covering member has regions having different densities.

5. The sanitary tampon according to claim 1, further comprising a thread sewing the absorber and the covering member together.

6. The sanitary tampon according to claim 1, wherein a diameter of the through hole on the inner side surface is smaller than a diameter of the through hole on the outer side surface.

* * * * *